United States Patent [19]

Sternfeld et al.

[11] Patent Number: 4,892,705
[45] Date of Patent: Jan. 9, 1990

[54] METHOD OF PRODUCING VAPOR FOR USE IN A VAPOR STERILIZING PROCESS

[75] Inventors: Hans J. Sternfeld, Jagsthausen; Karlheinz Wolfmüller, Eppingen-Adelshofen; Rodhardt Froese, Schömberg; Manfred Paulus, Pforzheim, all of Fed. Rep. of Germany

[73] Assignees: Fr. Kammerer GmbH, Huchenfeld; Deutsche Forschungs-und Versuchsaustalt fur luft-und Raumfahrt e.V., Bonn, both of Fed. Rep. of Germany

[21] Appl. No.: 178,882

[22] Filed: Apr. 4, 1988

Related U.S. Application Data

[63] Continuation of Ser. No. 836,969, Mar. 6, 1986, abandoned.

[30] Foreign Application Priority Data

Mar. 7, 1985 [DE] Fed. Rep. of Germany ....... 3508043

[51] Int. Cl.$^4$ ............................................. A61L 2/06
[52] U.S. Cl. .................... 422/26; 60/39.55; 422/1; 422/116; 422/204; 431/4; 431/170
[58] Field of Search ................ 422/1, 26, 204, 116; 431/4, 170; 60/39.55

[56] References Cited

U.S. PATENT DOCUMENTS

| 1,253,522 | 1/1918 | Patterson | 422/26 X |
| 3,836,328 | 9/1974 | Beauvais et al. | 422/26 |
| 4,385,661 | 5/1983 | Fox | 431/158 |
| 4,474,140 | 10/1984 | Sternfeld et al. | 431/170 |

FOREIGN PATENT DOCUMENTS

| 902171 | 12/1953 | Fed. Rep. of Germany . |
| 910826 | 5/1954 | Fed. Rep. of Germany . |
| 1301821 | 8/1969 | Fed. Rep. of Germany . |
| 2933932 | 3/1981 | Fed. Rep. of Germany . |
| 3508043 | 9/1986 | Fed. Rep. of Germany . |

Primary Examiner—Barry S. Richman
Assistant Examiner—Jill Johnston
Attorney, Agent, or Firm—Balogh, Osann, Kramer, Dvorak, Genova & Traub

[57] ABSTRACT

A method of generating a sterilizing vapor for use in a vapor sterilizing process, the method including the steps of burning a fuel selected from the group consisting of combustible gases and combustible aerosols, whereby hot combustion gases are generated, and introducing a liquid into said hot combustion gases, whereby the liquid is evaporated to form the sterilizing vapor.

5 Claims, 2 Drawing Sheets

METHOD OF PRODUCING VAPOR FOR USE IN A VAPOR STERILIZING PROCESS

This application is a continuation of application Ser. No. 836,969, filed Mar. 6, 1986, now abandoned.

BACKGROUND OF THE INVENTION

1. Field of the Invention

This invention relates to a method of producing vapor for use in a vapor sterilizing process.

2. Description of the Prior Art

Steam or another hot vapor is used for sterilizing mainly in medical engineering, pharmacy, food processing and biological technology.

Steam sterilizers are used for various purposes in medical engineering and their sizes differ in dependence on the intended purpose. The smallest devices are used to sterilize instruments in the offices of physicians and dentists and usually consist of small steam generators (autoclaves), which are electrically heated. Hospitals are usually equipped with larger systems for sterilizing medical utensils made of various materials, such as glass, metal, rubber, ceramics, plastics or pulp and for sterilizing textiles, such as disposable supplies or clothes. Such steam sterilizers are connected by fixedly installed annular steam lines to a central steam generator or are supplied with steam from separate steam generators, which are electrically heated.

Because the articles to be sterilized may consist of widely different materials, the temperatures which the materials will withstand vary widely, too, so that the sterilization must be effected under conditions selected in view of these requirements. In usual steam state generators for generating sterilizing steam the steam (or parameters) which can be achieved is determined by the boiling point curve of water. Because the conditions of sterilization which can be selected are restricted by the steam parameters which can be achieved (in the prior art the steam parameters can be varied only within a restricted range), the conditions of sterilization can be selected only within narrow limits. In the selection of the conditions the requirements for an optimum sterilization can be taken into account only as a secondary consideration.

Another disadvantage of the known steam generators for generating sterilizing steam resides in that it takes a relatively long time until the steam is available under the conditions required for sterilization.

The disadvantages described hereinbefore with reference to sterilization in medical engineering, by way of example, will also be encountered in connection with sterilization in pharmacy, in food processing and in biological technology, where a sterilization of biological reactors, fermenters and peripheral equipment, for instance, may be required.

SUMMARY OF THE INVENTION

An object of the invention is to provide for the generation of sterilizing steam by sterilizing vapor process in which steam or another vapor can be generated within a short time and which can be used to generate steam or another vapor under conditions which can readily be varied within wide limits.

This object is accomplished in accordance with the invention in that the sterilizing steam or another sterilizing vapor is generated in that a liquid to be evaporated is introduced into hot combustion gases, which have been produced by the combustion of a fuel which consists of a gas or aerosol.

In accordance with the invention the sterilizing steam or another sterilizing vapor is generated by a method which was originally developed for use in prime movers and in power plants, e.g., in power-generating units for generating power for satisfying peak demands (German Patent Specification Nos. 1,301,821 and 2,933,932). In the steam generators disclosed in the patent specifications, hydrogen gas and oxygen gas supplied through a nozzle unit into a combustion chamber and are burnt in the chamber to produce hot combustion gases, and additional water is injected to the hot combustion gases from pipelines which open into the combustion chamber. The injected water is evaporated in direct contact with the hot combustion gases and the resulting steam is discharged out of the combustion chamber under the high pressure maintained in the chamber.

That method can be used to generate steam under conditions which are represented by points disposed on or above the boiling point curve in the phase diagram of water. The steam condition will depend on the ratio of the rate at which the hydrogen-oxygen mixture is introduced into the combustion chamber to the rate at which water is injected. That ratio can be changed quickly and without difficulty through adjustable valves incorporated in the respective supply lines. As a result, the condition of the generated steam can also be changed within wide limits almost immediately.

Another important advantage of the invention resides in that steam or another vapor under the conditions required in a given case can be generated by the method in accordance with the invention virtually without a time lag, within about one second. It is no longer necessary to heat up the evaporator for a prolonged time, as was required with the known steam generators for generating sterilizing steam.

Any electric power required for the operation of a vapor generator in accordance with the invention will be extremely small because such power will be required only to control the evaporator rather than for the actual generation of vapor. Different from known steam sterilizers, sterilizers provide with evaporators operated in accordance with the invention may be operated even in regions where a supply of electric power for the generation of steam or another vapor is not ensured.

Besides, evaporators operated in accordance with the invention are highly efficient. Even very small evaporators can be used to generate steam or another vapor at high rates. For this reason and because steam or other vapors under preselected conditions can be made available within short time the method in accordance with the invention is particularly suitable for decentralized operations, particularly for mobile equipment.

Sterilizing vapor usually consists of pure steam, which is generated from distilled or deionized water. For special purposes, vapors of sterilizing liquids may be added to the steam. Besides, another sterilizing substance, such as formaldehyde, may be added to the water which is to be evaporated, and the mixed liquids may be used to generate steam. For certain applications the liquid to be evaporated may be free of water and may consist only of a different liquid, particularly of a liquid having a sterilizing activity, such as isopropanol.

The fuel suitably consists of hydrogen, which is burnt in the presence of oxygen or air to form water vapor. The combustion of hydrogen and oxygen in a stoichiometric ratio will result in generation of fully condensible water vapor.

Hydrogen and oxygen may be supplied to the combustion chamber in a non-stoichiometric ratio and, in particular, the hydrogen may be burnt in the presence of an excess of oxygen or in air. In that case the generated steam will contain incondensibles. Finally, a fuel gas other than hydrogen may be burnt, such as natural gas or other hydrocarbons, inclusive of liquid hydrocarbons, which may be atomized before they are burnt, provided that the combustion of the fuel gas does not result in combustion products which would not be desired for the sterilization.

An evaporator which is operated in accordance with the invention can be controlled to maintain the steam or another vapor in a sterilizer under conditions within very wide limits. Such conditions are defined by the pressure, temperature, humidity of the steam or other vapor and on the rate at which it is generated. This can be accomplished in that the rates at which the fuel and the oxygen are supplied and/or the rate at which the liquid to be evaporated is supplied are controlled e.g., by automatic control, so as to maintain the steam or other vapor under preselected conditions. An automatic control can be performed if sensors for detecting the vapor state (or parameters) are provided in the sterilizer and signals representing the vapor state (or parameters) are delivered by the sensors to a controller, which by means of adjustable valves controls the supply of the fuel, the oxygen and/or the liquid to be evaporated in such a manner that a preselected vapor state will be obtained. Within the scope of the invention, it is possible not only to maintain a constant vapor state during the sterilizing operation but to vary the vapor condition in accordance with a predetermined program in optimum adaptation to the material which is to be sterilized. By that program the controller incorporated in the feedback control system is supplied with signals which define time-dependent desired values for the vapor condition.

That control of the vapor condition will be particularly facilitated by the invention because an evaporator operated in accordance with the invention can be controlled virtually without a time lag.

DETAILED DESCRIPTION OF THE PREFERRED EMBODIMENTS

Illustrative embodiments of the invention are diagrammatically shown on the accompanying drawings.

Figure 1:
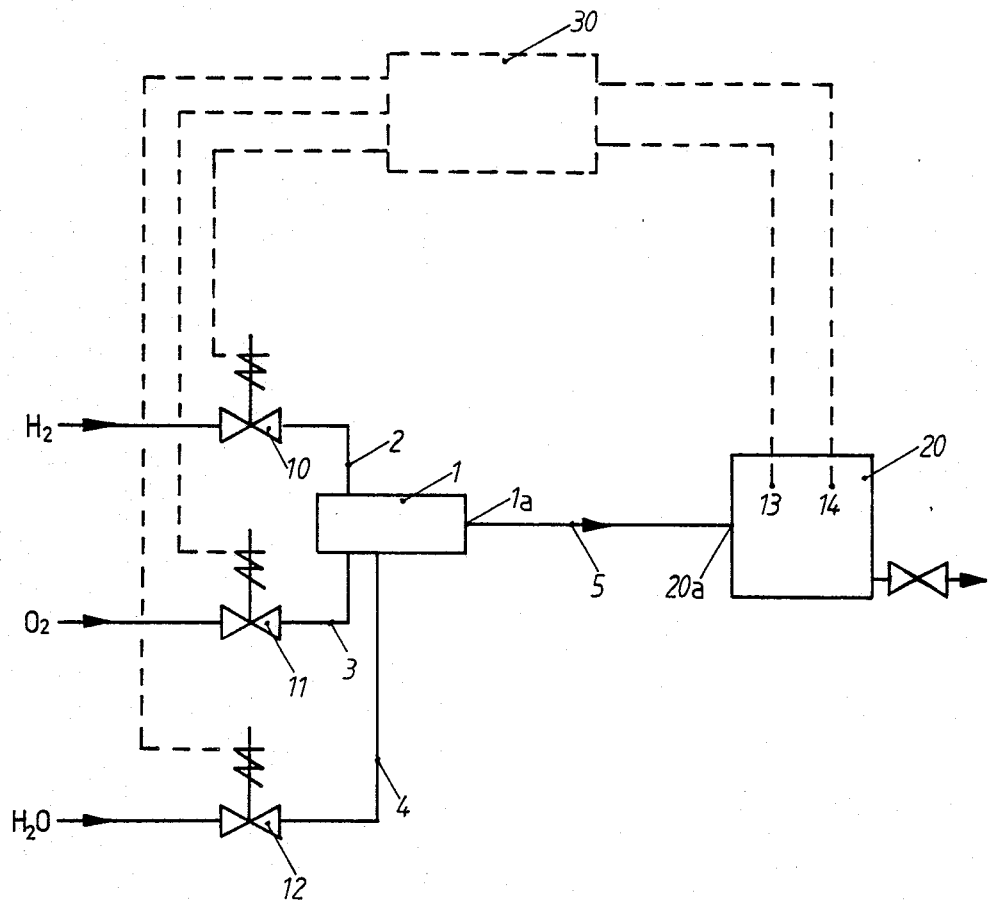
FIG. 1 is a block diagram illustrating the use of a steam generator for sterilizing a vessel and FIG. 2 is a block diagram illustrating the use of a plurality of steam generators for the steam sterilization of a plurality of chambers of a plant.

A steam generator 1 shown in FIG. 1 is supplied with hydrogen gas through a first supply line 2, with oxygen gas through a second supply line 3 and with water through a third supply line 4. In the steam generator 1, hydrogen and oxygen are burnt to generate steam, which is at a very high temperature and into which the water supplied through line 4 is injected in that the water is sprayed so that it is dispersed as uniformly as possible in the form of extremely fine droplets and that it will be evaporated virtually immediately in contact with the hot steam produced by the combustion.

The steam which has thus been generated is under a much higher pressure in the steam generator 1 than a steam which would be generated without the described reaction. Under that pressure the steam flows through an outlet 1a from the steam generator into a vessel 20, which contains the material to be sterilized.

The connection between the steam generator 1 and the container 20 may be constituted by a connecting line 5 or the outlet 1a of the steam generator may be directly joined to the inlet 20a of the vessel 20.

Hydrogen and oxygen gases are suitably supplied to the steam generator 1 from respective pressure containers. Each of said gases is supplied to the steam generator 1 under a desired pressure, which is controlled by a reducer valve, not shown. The supply lines 2 and 3 contain respective variable valves 10 and 11, which can be adjusted to vary the ratio of the rates at which hydrogen and oxygen are supplied to the steam generator 1. It is desirable always to supply hydrogen and oxygen at a stoichiometric ratio. In the steam generator 1, hydrogen and oxygen are burnt under controlled conditions. The combustion can be initiated by electric ignition or by catalysts.

The water which is supplied through line 4 may be introduced in any desired manner and may preferably be sprayed. The rate at which the water is supplied will depend on the required steam condition and is adjusted by means of a final control element 12, such as a valve, which is included in the supply line 4.

An automatic control may be used to cause the steam generator to deliver steam at a predetermined rate and to maintain a predetermined vapor state in the vessel 20. For that purpose, sensors 13 and 14 may be provided in the vessel 20 and may be used to detect predetermined variables of the steam, particularly its temperature and its pressure, and to deliver corresponding signals to a central controller 30, which is supplied with set point signals representing desired values of the variables monitored by the sensors 13 and 14. In the controller 30, the set point signals are compared with the output signals of the sensors 13, 14 and in case of deviations the controller 30 causes the flow rates to be controlled by the above-mentioned final control elements 10, 11 and 12. As any changes of the operating conditions of the steam generator can be detected within very short times of less than a second, the steam state (or parameters) can be changed most quickly and can be optimally adapted to the desired sterilization. The sequential changes of the steam state which are required for an optimum sterilization sequence may be indicated to the controller 30 by means of programmed control means, such as EPROMS.

A steam generator operating in accordance with the invention is superior to the known electrically heated steam generator for generating sterilizing steam in that the pressure and temperature of the steam can be independently and separately preset and steam parameters can be achieved within wide limits in the region of saturated and superheated steam. On the other hand, the parameters of the steam generated by conventional steam generators are restricted by the boiling point curve in the phase diagram of water.

It is apparent that the invention is unique in that it permits sterilizing processes to be optimized so that the best sterilizing effect can be achieved within a minimum of time and without an inherent restriction which is due to the design of the steam generator.

Figure 2:
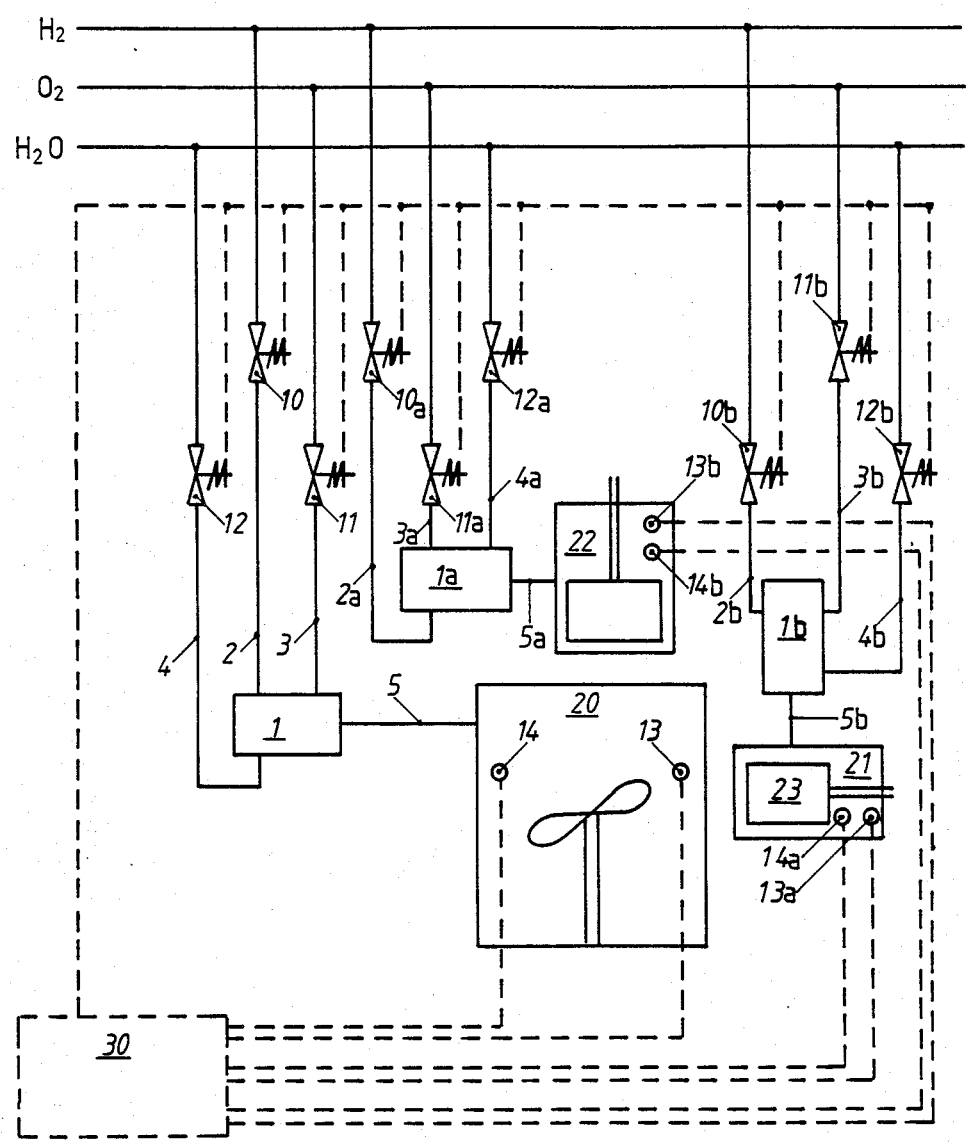

In the second embodiment shown in FIG. 2 parts which correspond to parts of the first embodiment are designated with the same reference characters as in FIG. 1. FIG. 2 shows a plant which comprises a plurality of chambers 20, 21, and 22, which are to be supplied with sterilizing steam. The plant shown in FIG. 2 may consist, e.g., of a fermenter plant used for biological technology. In such case the vessel 20 would be the fermenter proper, the chamber 21 would be, e.g., a lock chamber, through which a replaceable probe 23 can be moved into and out of the chamber 20, and the chamber 22 might be a part of a charging apparatus for charging the fermenter 20. In accordance with the fermentation sequence, the chambers 20, 21 and 22 must be sterilized at different times. For this reason, each of the chambers is connected by a supply line 5, 5a or 5b to a separate steam generator 1, 1a or 1b. Just as the steam generator of the first embodiment, each of the steam generators 1, 1a and 1b is connected to respective sources for a source of hydrogen gas, a source of oxygen gas and a source of water by means of supply lines 2, 3, 4; 2a, 3a, 4a, and 2b, 3b and 4b, which contain adjustable valves 10, 11, 12; 10a, 11a, 12a, and 10b, 11b, 12b, respectively said sources are common to all three steam generators.

Because steam generators operating in according with one invention permit the steam parameters to be varied within an extremely wide range, all three steam generators shown in FIG. 2 may have the same overall size. Just as in the first embodiment, the steam parameters may be controlled by a common controller 30, which monitors the steam parameters in chamber 20 by means of sensors 13, 14, in chamber 21 by means of sensors 13a and 14a, and in chamber 22 by means of sensors 13b and 14b. The valves 10, 11, 12; 10a, 11a, 12a; and 10b, 11b, 12b are preferably controlled separately so that the desired steam state is provided in each of the chambers 20, 21 and 22 at the proper time. In simpler arrangements, the various valves may be controlled by common final control elements.

Because the steam parameters, such as pressure, temperature, humidity and rate, can be controlled in adaptation to the instantaneous conditions in the fermenter, the total time required for sterilization may be much shorter than in the prior art and the sterilizing action can be improved.

As the method in accordance with the invention can be carried out by means of small, inexpensive steam generators, a plurality of steam generators can be economically used for sterilizing a fermenting plant and may be separately controlled. In addition to the actual fermenting chamber, other chambers of the plant, such as lock chambers, chambers for the introduction of electrodes or sensors, and sample-taking chambers, may be provided with separate stationary steam. Generators, which eliminate the previous need for expensive steam supply line systems, which are connected to a central steam generator and must be provided with separate control means for controlling the steam rates. Such supply line systems are expensive and liable to be deranged and involve a risk of maloperation, which is minimized in the process in accordance with the invention.

If in an arrangement which is similar to that of FIG. 2 a plurality of chambers, such as 20, 21, 22, are to be sterilized at different times and under different vapor parameters, the chambers may be supplied with sterilizing steam or with another sterilizing vapor from a common evaporator if the operation of the evaporator is controlled or automatically controlled in accordance with a suitable program so as to provide the proper vapor parameters for the sterilization of each of the chambers. In that case it will be particularly advantageous that the process in accordance with the invention permits a change of the vapor state to be effected within a very short time.

Evaporators operating in accordance with the invention can also be used for vapor sterilization in pharmacy and in conjunction with special sterilizers for sterilizing liquids such as milk or blood, which in the sterilizers are directly contacted by the steam or another vapor.

We claim:

1. A method of sterilizing objects comprising the steps of:
supplying hydrogen and oxygen at preselected supply rates in a stoichometric ratio into a combustion chamber;
burning the hydrogen with the said oxygen to generate hot combustion gases;
simultaneously introducing liquid water at a certain supply rate into said combustion gases whereby the water is evaporated to generate sterilizing steam;
introducing said sterilizing steam into a vessel housing said objects;
sensing vapor pressure and vapor temperature of said sterilizing steam; and
controlling the sterilization conditions by controlling the proportional supply rates of hydrogen and oxygen and independently thereof controlling the supply rate of the liquid water responsive to the sensed vapor pressure and vapor temperature thereby controlling the vapor supply rate, the vapor pressure and the vapor temperature independently and separately from each other.

2. The method according to claim 1, wherein said step of controlling said sterilization conditions is in accordance with a predetermined program.

3. The method according to claim 2, wherein said step of controlling said sterilization conditions is altering and in dependence on time in accordance with said predetermined program.

4. A method of sterilizing objects comprising the steps of:
supplying hydrogen and oxygen at preselected supply rates in a stoichometric ratio into a combustion chamber;
burning the hydrogen with the said oxygen to generate hot combustion gases;
simultaneously introducing liquid water at a certain supply rate into said combustion gases whereby the water is evaporated to generate sterilizing steam;
introducing said sterilizing steam into a vessel housing said objects;
sensing vapor pressure and vapor temperature of said sterilizing steam;
controlling the sterilization conditions by controlling the proportional supply rates of hydrogen and oxygen and independently thereof controlling the supply rate of the liquid water responsive to the sensed vapor pressure and vapor temperature thereby controlling the vapor supply rate, the vapor pressure and the vapor temperature independently and separately from each other; and
introducing a sterilizing substance into said water.

5. A method of sterilizing objects comprising the steps of:

supplying hydrogen and oxygen at preselected supply rates in a stoichometric ratio into a combustion chamber;

burning the hydrogen with the said oxygen to generate hot combustion gases;

simultaneously introducing liquid water at a certain supply rate into said combustion gases whereby the water is evaporated to generate sterilizing steam;

introducing said sterilizing steam into a vessel housing said objects;

sensing vapor pressure and vapor temperature of said sterilizing steam;

controlling the sterilization conditions by controlling the proportional supply rates of hydrogen and oxygen and independently thereof controlling the supply rate of the liquid water responsive to the sensed vapor pressure and vapor temperature thereby controlling the vapor supply rate, the vapor pressure and the vapor temperature independently and separately from each other; and introducing a gaseous sterilizing medium into said combustion gases.

* * * * *